US00PP10598P

United States Patent [19]

Alexander

[11] Patent Number: Plant 10,598

[45] Date of Patent: Sep. 8, 1998

[54] LYSIMACHIA PUNCTATA PLANT NAMED 'ALEXANDER'

[76] Inventor: Pauline Alexander, 40 Knapton Lane, Acomb, York Y02 5PU, United Kingdom

[21] Appl. No.: 828,653

[22] Filed: Mar. 31, 1997

[51] Int. Cl.[6] ..... A01H 5/00

[52] U.S. Cl. ..... Plt./68.1

[58] Field of Search ..... Plt./68.1

*Primary Examiner*—Howard J. Locker
*Assistant Examiner*—Melissa L. Kimball
*Attorney, Agent, or Firm*—C. A. Whealy

[57] ABSTRACT

A distinct cultivar of *Lysimachia punctata* plant named 'Alexander', characterized by its upright, vigorous and freely branching growth habit; green and cream-white variegated foliage; numerous yellow flowers that flower continuously throughout the summer; and good garden performance.

1 Drawing Sheet

The present invention relates to a new and distinct cultivar of Lysimachia plant, botanically known as *Lysimachia punctata* and refered to by the cultivar name Alexander. The new Lysimachia is named in honor of the inventor's late husband, Mr. Donald Stuart Alexander. The new cultivar is a naturally-occurring leaf color mutation of the species *Lysimachia punctata*. In the summer of 1990, the new cultivar was discovered by the inventor in a cultivated outdoor area in Acomb, York, United Kingdom, within a population of plants of the species *Lysimachia punctata*.

Asexual reproduction of the new cultivar by terminal cuttings taken at Walburton, Arundel, Sussex, United Kingdom, has shown that the unique features of this new Lysimachia are stable and reproduced true to type in successive generations.

The following traits have been repeatedly observed and are determined to be the unique characteristics of 'Alexander'. These characteristics in combination distinguish 'Alexander' as a new and distinct cultivar:

1. Upright, vigorous and freely branching growth habit.
2. Green and cream-white variegated foliage.
3. Numerous yellow flowers that flower continuously throughout the summer.
4. Good garden performance.

The cultivar Alexander has not been observed under all possible environmental conditions. The phenotype may vary somewhat with variations in environment such as temperature and light intensity without, however, any variance in genotype.

Plants of the new Lysimachia are similar to the parent species *Lysimachia punctata* in all characteristics with the exception of leaf and sepal variegation. A detailed comparison of the differences between plants of the new Lysimachia and the species *Lysimachia punctata*appears in Chart A at the end of the specification.

The accompanying colored photograph illustrates the overall appearance of the new cultivar, showing the colors as true as it is reasonably possible to obtain in colored reproductions of this type. The photograph comprises a top perspective view of typical flowering plants of 'Alexander' in a garden setting. Foliage and flower colors in the photograph may appear different from the actual colors due to light reflectance.

In the following description, color references are made to The Royal Horticultural Society Colour Chart except where general terms of ordinary dictionary significance are used. The following observations and measurements describe plants flowered in a glass greenhouse in February in Walburton, Arundel, Sussex, United Kingdom. Day temperatures ranged from 16 to 21° C and night temperatures ranged from 10 to 16° C. Plants were exposed to a 20-hour daylength until January. Measurements and numerical values represent ranges or averages for six typical flowering plants.

Botanical classification: *Lysimachia punctata* cultivar Alexander.

Parentage: Naturally-occurring leaf color mutation of the species *Lysimachia punctata*.

Propagation:

*Type.*—Terminal tip cuttings.

*Time to rooting.*—To initiation:About 10 days at 20° C. To development: About 14 days at 20° C.

*Rooting habit.*—Fine, fibrous and branced.

Plant description:

*Appearance.*—Upright perennial herbaceous garden plant. Vigorous and freely branching. Appropriate for 1.5 1 or larger containers.

*Plant height.*—Usually 45 to 90 cm.

*Lateral branches.*—Quantity: Up to 10. Diameter: 1.5 to 6 mm. Internode length: 1.3 to 3.8 cm. Stem color: 138A to 138C. Texture: Pubescent with longitudinal ridges.

*Foliage description.*—Leaves opposite, occasionally alternate. Quantity: Up to 30 per lateral branch. Leaf shape: Ovate. Leaf length: 2.5 to 10 cm. Leaf width: 1.9 to 5 cm. Leaf apex: Acute. Leaf base: Obtuse/cuneate. Leaf texture: Pubescent and rough. Petiole length: 3 to 6 mm. Petiole diameter: 1.5 to 3 mm. Color: Young foliage adaxial surface: Center, 138A/138B; margin, 158B/158C. Young foliage abaxial surface: Center, 139C/138C; margin, 158B/158C. Fully expanded foliage adaxial surface: Center, 147A/138A; margin 158A/158C. Fully expanded foliage abaxial surface: Center, 147B/138B; margin, 158B/158C. Vein color, adaxial surface: 138B. Vein color, abaxial surfac: 138C.

Flower description:

*Appearance.*—Single flowers arranged on spikes arising from leaf axils. Flowers face outward and positioned on all sides of the flower stem. Bell-shaped flowers at base flairing to a star. Flowers long-lasting, typically 5 to 7 days. Flowers self-cleaning, not persistent.

*Natural flowering season.*—Under natural conditions, plants flower continuously from late June through August in the Northern Hemisphere.

*Quantity.* —Typically 20 to 30 flowers per spike with ususally 3 to 10 flowers open at one time.

*Flower size.*—Diameter: About 2.5 cm. Depth (height): 1.3 to 1.9 cm.

*Petals.*—Appearance: Dull, with faint reddish longitudinal veining. Quantity: Five. Shape: Ovate. Length: 1.3 to 1.9 cm. Width: About 1 cm. Apex: Acute. Margin: Edged with glandular hairs. Color, when opening, adaxial surface: 12A/14B. Color, when opening, abaxial surface: 12A. Color, fully opened, adaxial surface: 12A/14B. Color, fully opened, abaxial surface: 12A.

*Sepals.*—Quantity: Five. Shape: Linear/lanceolate. Calyx length: 3 to 5 mm. Calyx width: About 3 mm. Apex: Pointed. Margin: Pubescent. Texture: Rough, pubescent. Color, adaxial surface: Center, 138C; margin 158C. Color, abaxial surface: Center, 138C; margin 158C.

*Peduncle.*—Aspect: Flexible, 30° to stem. Length: 1.25 to 5 cm. Color: 138A to 138C.

*Flower bud.*—Length: About 1.25 cm. Diameter: About 3 mm. Color: 12A.

*Reproductive organs.*—Androecium: Stamen number: Five. Anthers: Length: About 1.5 mm. Width: About 0.75 mm. Color: 21A. Pollen: Moderate, 21A in color. Gynoecium: Pistil number: One. Pistil length: 3 to 5 mm. Stigma color: 139B. Style color: 194B to 194D. Style length: 3 to 5 mm. Ovary number: One. Ovary color: 194A/196D.

*Seed.*—Occurrence: Occasionally. Length: About 0.15 mm. Width: About 0.15 mm. Color: 165A.

Disease resistance: Not susceptible to known Lysimachia diseases when grown under commerical greenhouse conditions.

CHART A

| CHARACTERISTIC | 'ALEXANDER' | *LYSIMACHIA PUNCTATA* |
|---|---|---|
| YOUNG LEAF COLOR, ADAXIAL SURFACE | Center, 138A/138B Margin, 158B/158C | 138A/138B |
| YOUNG LEAF COLOR, ABAXIAL SURFACE | Center, 139C/138C Margin, 158B/158C | 139C/138C |
| MATURE LEAF COLOR, ADAXIAL SURFACE | Center, 147A/138A Margin, 158A/158C | 138A/138B |
| MATURE LEAF COLOR, ABAXIAL SURFACE | Center, 147B/138B Margin, 158B/158C | 139C/138C |
| SEPAL COLOR, ADAXIAL SURFACE | Center, 138C Margin, 158C | 138C |
| SEPAL COLOR, ABAXIAL SURFACE | Center, 138C Margin, 158C | 138C |

It is claimed:

1. A new and distinct cultivar of *Lysimachia punctata* plant named 'Alexander', as illustrated and described.

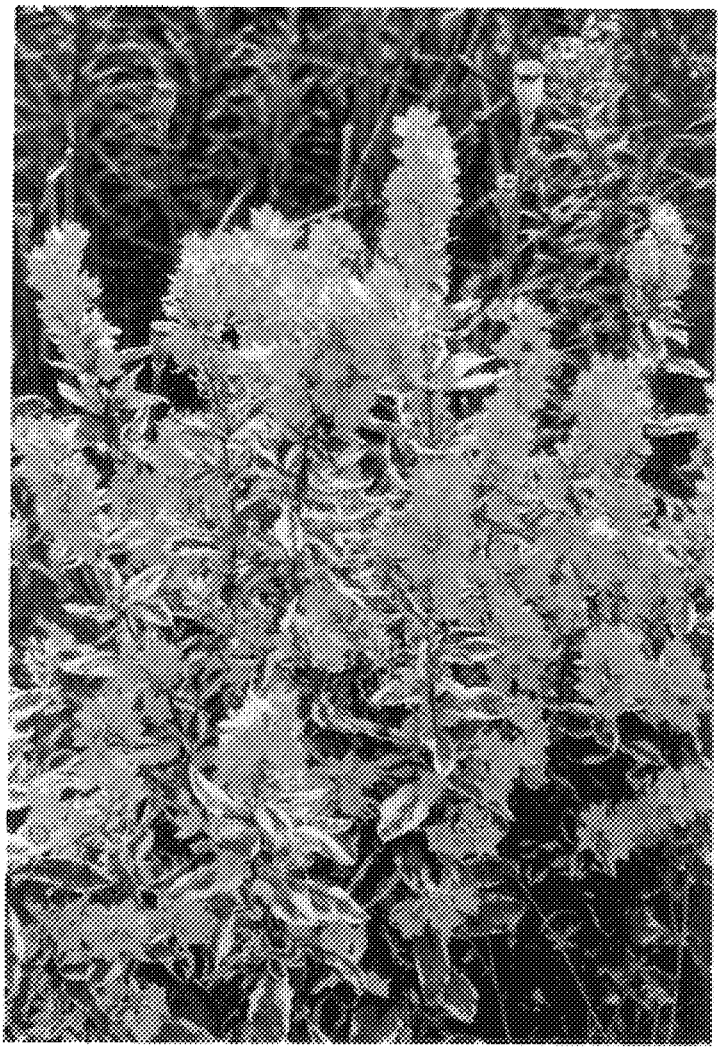

* * * * *